(12) United States Patent
Makower

(10) Patent No.: US 7,179,270 B2
(45) Date of Patent: Feb. 20, 2007

(54) METHODS FOR BYPASSING TOTAL OR NEAR-TOTAL OBSTRUCTIONS IN ARTERIES OR OTHER ANATOMICAL CONDUITS

(75) Inventor: Joshua Makower, Los Altos, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 644 days.

(21) Appl. No.: 10/370,231

(22) Filed: Feb. 19, 2003

(65) Prior Publication Data

US 2003/0236542 A1 Dec. 25, 2003

Related U.S. Application Data

(60) Continuation of application No. 09/267,943, filed on Mar. 11, 1999, now Pat. No. 6,231,587, which is a division of application No. 09/179,809, filed on Oct. 27, 1998, now Pat. No. 6,068,638, which is a continuation of application No. 08/730,496, filed on Oct. 11, 1996, now Pat. No. 5,830,222.

(60) Provisional application No. 60/005,164, filed on Oct. 13, 1995.

(51) Int. Cl.
*A61M 29/00* (2006.01)

(52) U.S. Cl. .................................................. 606/159

(58) Field of Classification Search ................ 606/159, 606/191–198; 623/1.11, 1.12, 1.2
See application file for complete search history.

(56) References Cited

U.S. PATENT DOCUMENTS 5,287,861 A * 2/1994 Wilk ........................... 128/898

(Continued)

FOREIGN PATENT DOCUMENTS

WO WO 00/18323 4/2000

OTHER PUBLICATIONS

Pokrovsky, A.V., et al., Arterialization of the Foot Venous System in the Treatment of the Critical Lower Libmb Ischemia and Distal Arterial Bed Occlusion, J. Cardiovasc Surg 1998; 39(Suppl. 1 to 1):171-8.
Chevalier, Bernard, et al., Chronic Total Occlusion, The Paris Course on Revascularization, May 2000, pp. 131-148.

*Primary Examiner*—Kevin T. Truong

(57) ABSTRACT

Methods for bypassing total or near-total obstructions in arteries or other anatomical conduits. A guidewire is advanced through the lumen of the artery or anatomical conduit upstream of the obstruction and past the obstruction. In navigating past the obstruction, this guidewire may advance through tissue that is located within the wall of the artery or anatomical conduit and/or through tissue that is located outside of the wall of the artery or anatomical conduit. After this guidewire has been advanced past the obstruction, a penetrating catheter that is equipped with an orientation element is advanced over that guidewire. The orientation element is then used to aim a penetrator back into the lumen of the obstructed artery or conduit, downstream of the obstruction. The penetrator is then advanced into the lumen of the obstructed artery or conduit, downstream of the obstruction, and a final guidewire is advanced through the penetrator and into the lumen of the artery or conduit downstream of the obstruction. The catheter (and the guidewire that was initially used to pass the obstruction) may then be removed, leaving the final guidewire in place. A balloon or other tract enlarging device may be used to dilate or otherwise enlarge the bypass tract through which the final guidewire extends. Also, a covered or uncovered stent may be placed within the tract to facilitate flow from the lumen of the artery or anatomical conduit upstream of the obstruction, through the newly created bypass tract and back into the lumen of the artery or anatomical conduit downstream of the obstruction.

8 Claims, 9 Drawing Sheets

U.S. PATENT DOCUMENTS

| | | | |
|---|---|---|---|
| 5,345,940 A * | 9/1994 | Seward et al. | 600/463 |
| 5,429,144 A * | 7/1995 | Wilk | 128/898 |
| 5,456,694 A * | 10/1995 | Marin et al. | 604/103.05 |
| 5,558,091 A | 9/1996 | Acker et al. | |
| 5,562,619 A * | 10/1996 | Mirarchi et al. | 604/264 |
| 5,599,346 A * | 2/1997 | Edwards et al. | 606/38 |
| 5,636,644 A * | 6/1997 | Hart et al. | 128/897 |
| 5,654,864 A | 8/1997 | Ritter | |
| 5,752,513 A | 5/1998 | Acker et al. | |
| 5,820,568 A | 10/1998 | Willis | |
| 5,830,222 A * | 11/1998 | Makower | 604/99.03 |
| 5,833,608 A | 11/1998 | Acker | |
| 5,928,248 A | 7/1999 | Acker | |
| 5,931,818 A | 8/1999 | Werp et al. | |
| 6,068,638 A * | 5/2000 | Makower | 606/159 |
| 6,159,225 A * | 12/2000 | Makower | 606/155 |
| 6,190,353 B1 * | 2/2001 | Makower et al. | 600/137 |
| 6,231,587 B1 * | 5/2001 | Makower | 606/108 |
| 6,464,665 B1 * | 10/2002 | Heuser | 606/159 |

\* cited by examiner

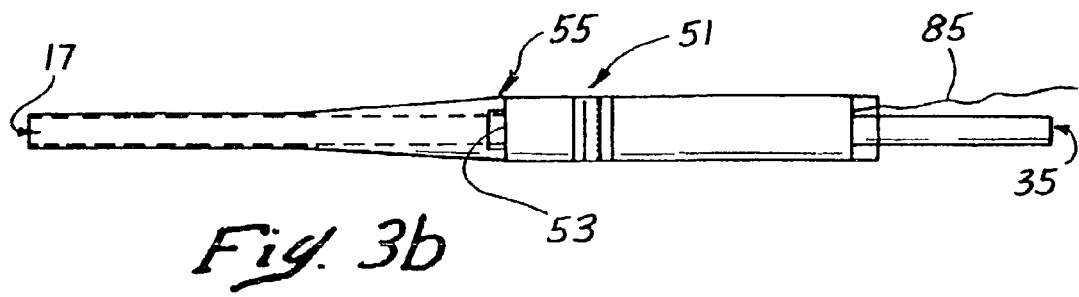
Fig. 3b
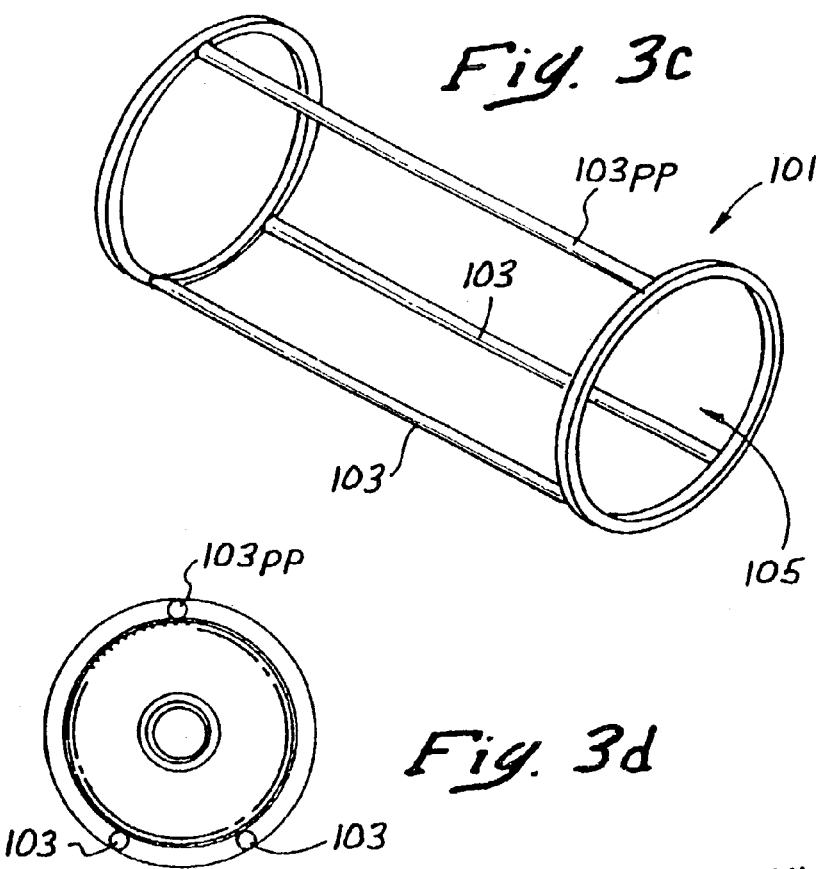
Fig. 3c
Fig. 3d
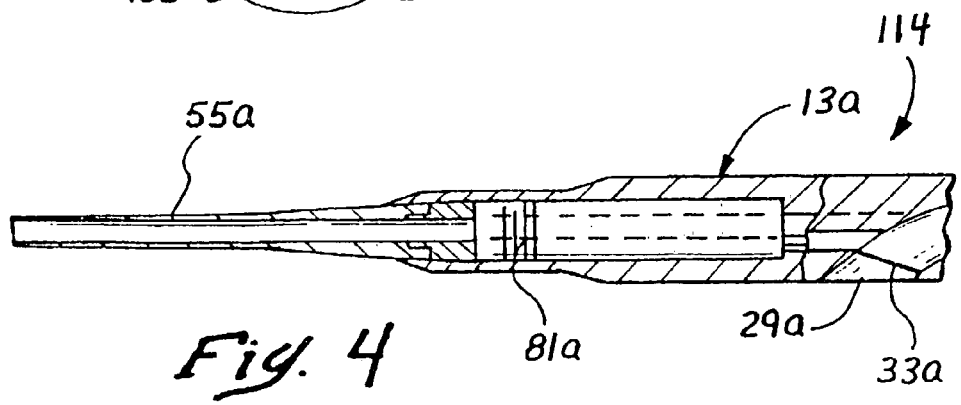
Fig. 4

METHODS FOR BYPASSING TOTAL OR NEAR-TOTAL OBSTRUCTIONS IN ARTERIES OR OTHER ANATOMICAL CONDUITS

RELATED APPLICATION

This is a continuation of application Ser. No. 09/267,943 filed Mar. 11, 1999 and now issued as U.S. Pat. No. 6,231,587, which is a divisional of application Ser. No. 09/179,809 filed on Oct. 27, 1998 and now issued as U.S. Pat. No. 6,068,638, which was a continuation of application Ser. No. 08/730,496 filed Oct. 11, 1996 and now issued as U.S. Pat. No. 5,830,222, which claimed priority to provisional application No. 60/005,164 filed Oct. 13, 1995.

BACKGROUND OF THE INVENTION

Total or near-total occlusions in arteries can prevent all or nearly all of the blood flow through the affected arteries. It has been estimated that 5% to 15% of patients on whom percutaneous coronary angioplasty (PTCA) is attempted are found to have chronic total occlusions (CTO's) of at least one coronary artery. Chevalier, B. et al., *Chronic Total Occlusion,* The Paris Course on Revascularization, Pages 131–148 (May 2000) In patients who suffer from coronary CTO's, the successful performance of a PTCA is a technical challenge. The factor that is most determinative of whether the interventionalist can successfully perform PTCA on patient who presents with a coronary CTO is the interventionalist's ability (or inability) to advance a suitable guidewire from a position within the lumen of the artery upstream of the lesion, across the lesion (i.e., either through the lesion or around it), and then back into the artery lumen at a location downstream of the lesion.

In some instances, such as where the occlusive matter is soft or where the occlusion is less than total, the guidewire can simply be pushed through the occlusive matter itself, thereby allowing the guidewire to remain within the artery lumen. However, in other cases, such as where the artery is totally occluded by hard, calcified atherosclerotic plaque, the guidewire may tend to deviate to one side and penetrate through the intima of the artery, thereby creating a neo-lumen through the sub-intimal space (i.e., within the wall of the artery between the intima and adventitia). In these cases, after the distal end of the guidewire has been advanced to a position distal to the lesion, it is then necessary to divert or steer the guidewire from the sub-intimal space back into the lumen of the artery at a location downstream of the lesion. This process of causing the guidewire to reenter the artery lumen is often difficult and others have proposed various means for dealing with such problem. For example, PCT International Publication No. WO 00/18323 describe techniques where a catheter that has a through lumen terminating distally in a laterally directed outlet port is advanced into the sub-intimal space past the lesion and a penetrator or guidewire is then advanced through the catheter, out of the laterally directed outlet port, and back into the lumen of the artery. WO 00/18323 further states that optionally a wire may be passed through a lumen of the catheter and that such wire may further comprise an imaging apparatus such as an ultrasonic imaging means. Also, WO 00/18323 states that the catheter may include a marker near its distal end that is visible on fluoroscopy and that such marker may be configured to permit visual determination of the rotational orientation of the distal end of the catheter when viewed as a two-dimensional fluoroscopic image. However WO 00/18323 does not describe any means for correlating the rotational orientation of the catheter to the trajectory on which the penetrator or guidewire will subsequently advance. A number of variable can affect the trajectory on which the penetrator or guidewire will advance, including the location of the outlet aperture from which the penetrator or guidewire exits the catheter body, the density and resistance of the tissue through which the penetrator or guidewire advances and any bias, shape or curvature that the penetrator or guidewire will assume after it is no longer constrained by the catheter.

Another approach to bypassing a CTO, as described in U.S. Pat. No. 6,068,638 (Makower), U.S. Pat. No. 5,830,222 (Makower) and U.S. Pat. No. 6,190,353B1 (Makower, et al.) utilizes a tissue penetrating catheter device that has an on board guidance element that allows a tubular penetrator cannula to penetrate outwardly through the intima of the artery wall upstream of the lesion after which a member is advanced trough the cannula and bores through tissue located outside of the vessel's intima, to a position distal to the obstructive lesion, and then reenters the lumen of the artery at a location downstream of the lesion. Tissue penetrating catheters of this type, having on-board guidance and/or orientation capabilities and penetrator cannulas that are advanceable laterally from the catheter body, have previously been devised. (Transaccess® catheters by Transvascular,® Inc., Menlo Park, Calif.)

There exists a need in the art for the development of new and better techniques for catheter-based treatment of CTO and other total or near-total obstruction of arteries or other anatomical conduits, especially with respect to improving the available techniques for causing a guidewire to reenter the lumen of an artery from a location within the sub-intimal space or even outside of the artery wall and for facilitating verification of the intended re-entry into the artery lumen and prompt delivery of arterial blood or some other oxygenated perfusate to tissues that would normally receive arterial blood flow from the obstructed artery.

SUMMARY OF THE INVENTION

The present invention provides methods for bypassing total or near total occlusions of arteries or other anatomical conduits through the use of catheters that include a) penetrators that are advanceable from the catheter, such penetrators having lumens that extend therethrough such that a guidewire can be advanced through the penetrator, blood or marker fluid can be withdrawn through the penetrator lumen to verify that the distal end of the penetrator is in fact positioned in the artery lumen and/or substance(s) such as radiographic contrast medium, therapeutic or diagnostic agents or oxygenated perfusate may be injected through the lumen of the penetrator and b) one or more orientation element(s) (e.g., marking(s), imaging apparatus, sensor(s), emitter(s) and/or combinations thereof) that are useable to determine the rotational orientation of the catheter within the body relative to the trajectory on which the penetrator will subsequently advance thereby enabling operator to precisely position and orient the catheter before advancement of the penetrator such that the penetrator will accurately reenter the lumen of the artery or other conduit from a location within or outside of the wall of the artery or other conduit.

In accordance with one embodiment of the invention, there is provided a method for bypassing an obstruction in an artery or other anatomical conduit by first advancing a first elongate member (e.g., a cardiovascular guidewire) into the lumen of the obstructed artery or body conduit to a position where its distal end is proximal to the obstruction. Thereafter, using techniques known in the prior art, the operator maneuvers the first elongate member within or outside of the wall of the artery or other luminal anatomical structure and past the obstruction position where the distal end of the first elongate member is distal to the obstruction and outside of the lumen of the anatomical conduit. Thereafter, a penetrating catheter that comprises i) an elongate, flexible catheter body having a distal end, ii) a lumen extending longitudinally through at least a distal portion of the catheter body to permit the catheter device to be advanced over an elongate member iii) a penetration member or penetrator that penetrates into or through the wall of the anatomical conduit in which the catheter body is positioned and iv) an orientation element useable to enable the operator to determine the rotational orientation of the catheter body within the anatomical conduit so that the penetration member may be aimed at a target location, is advanced over the first elongate member to a position where the distal end of the catheter body is positioned outside of the lumen of the anatomical conduit, distal to the obstruction. Thereafter, the catheter body is rotationally oriented with the aid of the orientation element such that, when the penetration member is subsequently advanced from the catheter body, the penetration member will enter the lumen of the anatomical conduit distal to the obstruction. After the catheter has been placed in such rotational orientation, the penetration member is advanced into the lumen of the anatomical conduit. A second elongate member (e.g., a cardiovascular guidewire) may then be passed through the lumen of the penetration member and into the lumen of the anatomical conduit. Thereafter, the penetration member is retracted into the catheter and the catheter is removed, leaving the second elongate member in place. The obstruction is thereby crossed. The tract formed around the obstruction may then be enlarged and/or stented in accordance with well known techniques to allow flow (e.g., blood flow) around the obstruction.

In accordance with another embodiment of the invention, there is provided another method for bypassing an obstruction in an artery or other anatomical conduit. In this embodiment of the method, a first elongate member (e.g., a cardiovascular guidewire) is initially advanced into the anatomical conduit proximal to the obstruction. Thereafter, a penetrating catheter that comprises i) an elongate, flexible catheter body having a distal end, ii) a lumen extending longitudinally through at least a distal portion of the catheter body to permit the catheter device to be advanced over an elongate member iii) a penetration member or penetrator that penetrates into or through the wall of the anatomical conduit in which the catheter body is positioned and iv) an orientation element useable to enable the operator to determine the rotational orientation of the catheter body within the anatomical conduit so that the penetration member may be aimed at a target location, is advanced over the first elongate member to a position where the distal end of the catheter body is positioned within the lumen of the anatomical conduit proximal to the obstruction. If desired, the orientation element may optionally be used at this time to rotationally orient the catheter within the lumen of the anatomical conduit. Thereafter, the penetration member is advanced from the catheter and into or through the wall of the anatomical conduit. A second elongate member (e.g., a second cardiovascular guidewire) is then advanced through the penetrator, out of the distal end of the penetrator and through tissue located within or outside of the wall of the anatomical conduit, to a position where the distal end of the second elongate member is distal to the obstruction but still outside of the lumen of the anatomical conduit. The penetrator is retracted into the catheter and the catheter is then removed, leaving the second elongate member in place. The penetrating catheter is then reinserted and advanced over the second elongate member to a position where the distal end of the catheter device is distal to the obstruction and outside of the lumen of the anatomical conduit. The orientation element is then used to rotationally orient the catheter such that, when the penetration member is subsequently advanced from the catheter body, the penetration member will enter the lumen of the anatomical conduit distal to the obstruction. Thereafter, the penetration member is advanced from the catheter and into the lumen of the anatomical conduit, downstream of the obstruction. A third elongate member (e.g., a cardiovascular guidewire) may then be passed through the lumen of the penetration member and into the lumen of the anatomical conduit. Thereafter, the penetration member is retracted into the catheter and the catheter is removed, leaving the third elongate member in place. The obstruction is thereby crossed. The tract formed around the obstruction may then be enlarged and/or stented in accordance with well known techniques to allow flow (e.g., blood flow) around the obstruction.

In cases where the anatomical conduit is an obstructed artery, the bypass tract will be formed outside of the intima of the artery. Sometimes, the bypass tract will be entirely within the artery wall. Other times, the bypass tract may penetrate outside of the artery wall into tissue or space adjacent to the artery.

BRIEF DESCRIPTION OF THE DRAWINGS

FIG. 3b is an enlarged elevational view showing the distal tip section of the catheter.

FIG. 3c is a perspective view of the marker structure of the catheter embodiment shown in FIGS. 3a–3b.

FIG. 3d is a cross sectional view through the distal portion of the catheter of FIG. 2.

DETAILED DESCRIPTION OF PREFERRED EMBODIMENTS

The following detailed description, and the drawings to which it refers, are provided for the purpose of describing and illustrating certain examples or embodiments of the invention only and are not intended to exhaustively describe or show all possible embodiments or examples of the invention.

Figure 1:
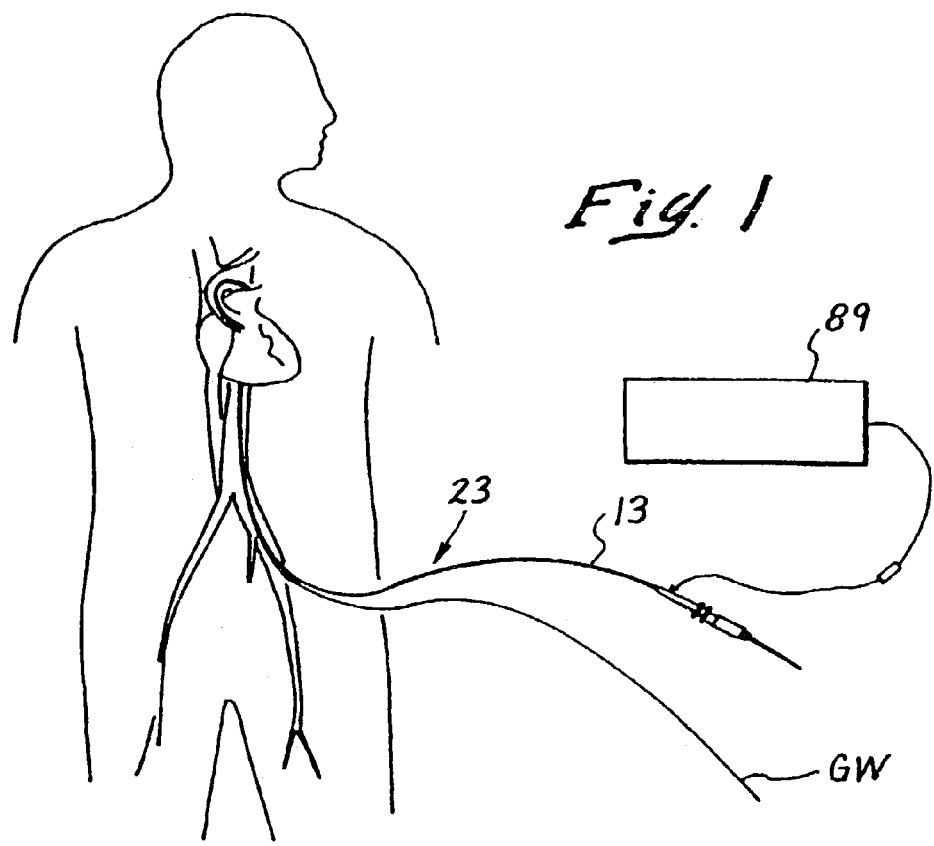
FIG. 1 is a schematic showing of a human patient who is undergoing a procedure for bypassing a total or near total obstruction of a coronary artery, in accordance with the present invention.
Figure 2:
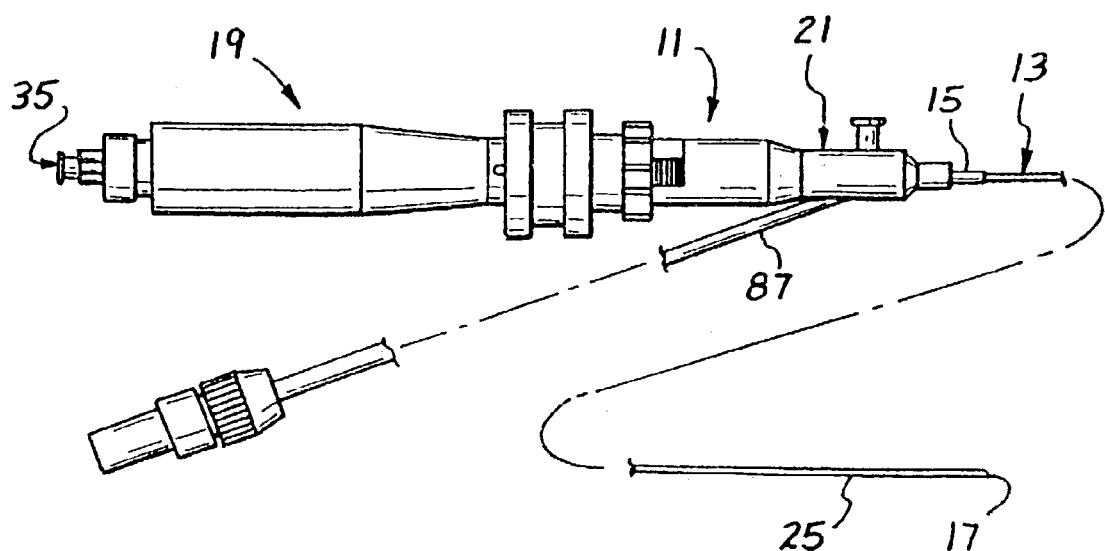
FIG. 2 is a broken, side view of one embodiment of a penetrating catheter device useable for performing the methods of the present invention.

A. The Penetrating Catheter:

FIG. 2 shows a penetration catheter 11 that is equipped for precise rotational orientation and aiming of its penetrator 85, in accordance with the teachings of this invention, while FIG. 1 shows the catheter 11 in use on a human patient. In the embodiment illustrated, the catheter 11 includes an elongated catheter body 13 having a proximal end 15, a distal end 17, a handle 19 and a hub 21 coupled to the proximal end of the catheter body 15 and to the handle. The handle 19 may also serve as a controller for use in advancing and retracting the penetrating instrument, such as a tissue penetrator 85 described more fully below.

The Catheter Body

Figure 3:
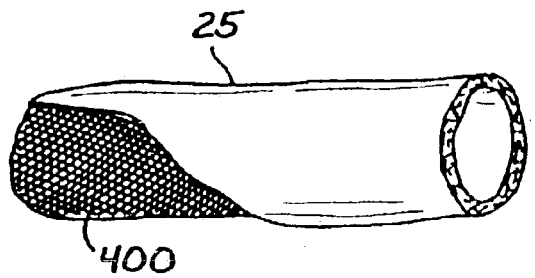
FIG. 3 is an enlarged, cut-away view of the wire braid formed within the distal section of the catheter body.
Figure 3A:
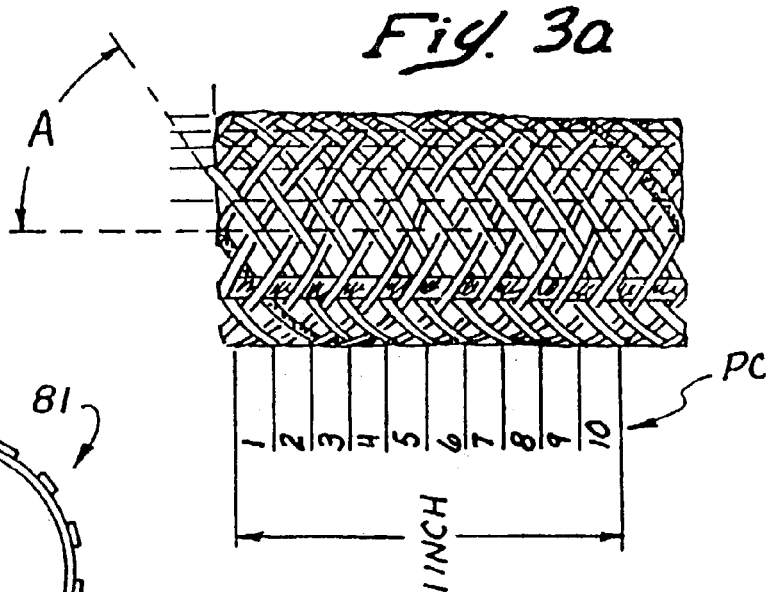
FIG. 3a is a diagram of a catheter braid illustrating the braid angle and pick count of the braid.

The catheter body 13 includes a relatively rigid proximal section 23 shown in FIG. 2 which may be constructed, for example, of a metal hypo tube and an elongated flexible distal section or region 25 suitably joined to the proximal section. A hand piece 19 is attached to the proximal end of the proximal section 23, as shown. In the preferred embodiment the hand piece 19 and proximal section 23 are approximately 100 cm in length. The flexible distal section 25 may incorporate a reinforcement member such as a wire braid 400 as shown in FIGS. 3 and 3a and, in the preferred embodiment is approximately 30 cm in length. The braid 400 terminates approximately 3 cm from the distal end 17.

It has been determined that material expansion and changes in the physical properties of certain materials may occur after the catheter 11 is inserted into the patient's body and warmed from room temperature to body temperature. This material expansion and changes in the physical properties of certain materials can result in variation in the tolerances and sizing of the catheter 11 (e.g. elongation or shrinking) and can thus give rise to an unwanted modification of the position of the tissue penetrating member 85. This could, in at least some cases, interfere with the precise aiming and advancement of the tissue penetrating member as desired. FIG. 3a″ illustrates the braid angle A and pick count PC of the catheter braid 400. The "pick count" PC of the braid is, as is well known in the art, a function of the braid angle A (i.e., the greater the braid angle the more picks per inch). Also, the torque transmission and stiffness of the braided distal section 25 is a function of the braid angle (i.e., a braid angle of 90 degrees provides maximum torque transfer and a braid angle of 0 degrees provides minimum torque transfer). Typically, cardiovascular catheters used in procedures such as those described herein utilizing a venous approach have braid angles A that result in a pick count of 50–70 picks per inch. However, applicant has determined that by decreasing the braid angle A of the braid 400 within the distal section 25 of the catheter 11 to result in a lower pick count, it is possible to minimize or eliminate the unwanted longitudinal expansion of the catheter 11 and/or its components, while retaining sufficient torque transmission and acceptable stiffness to accomplish the procedures for which the catheter 11 is intended (examples of such procedures are illustrated in FIGS. 7a–8d herebelow). This variation in braid angle or picks per inch may vary depending on the material of construction of the catheter and/or the braid fiber, and the diameter of the catheter body.

In instances where the catheter 11 is intended for use in a coronary artery, at least the distal section 25 of the catheter 11 is sized to be received within a coronary artery, and therefore can be received within either a coronary artery or a coronary vein or other lumens of equal diameter. The catheter body section 13 has a penetrator lumen 27 that terminates distally at an exit location or exit port 29 (FIG. 3a) on a peripheral wall 31 of the catheter body. The penetrator lumen 27 extends proximally from the exit port 29 to the proximal end 15 of the catheter body 13 and communicates with the interior of the handle 19 through the hub 21. The penetrator lumen 27 contains or is adapted to receive an instrument, such as the tissue penetrator 85 shown in FIG. 3a, for penetrating out of the blood vessel in which the catheter 11 resides (i.e., the "resident vessel") and to a target location. The exit port 29 is preferably located a short distance proximally of the distal end 17. A radiopaque marker 33 is mounted on the lumen 27 adjacent the exit port 29.

The catheter body 13 also has a guidewire lumen 35 which extends to the distal end 17 of the catheter body 15. In this embodiment, the guidewire lumen 35 extends proximally to an inlet port in the peripheral wall of the catheter body 13 closely adjacent the proximal section 23. The catheter body 13 also has a lead lumen for a purpose described below.

A major section 51 of the catheter body 13 terminates distally in a distal opening 53, and the catheter body includes a distal tip section 55 of soft, flexible, biocompatible material (FIG. 3b). A proximal portion of the distal tip section 55 is received in the distal opening 53 and a distal portion of the distal tip section extends distally to the distal end 17.

For some applications such as those where it is desirable for more of the distal portion of the catheter to have additional flexibility, metal hypotube of the proximal section 23 may terminate a desired distance from the distal tip (e.g., 30 cm proximal to the distal tip) such that the entire portion of the catheter distal to the location at which the metal hypotube ends (e.g., the distal 30 cm) will be more flexible than the portion of the shaft proximal thereto that does incorporate the hypotube.

Phased Array Transducer

Figure 4A:
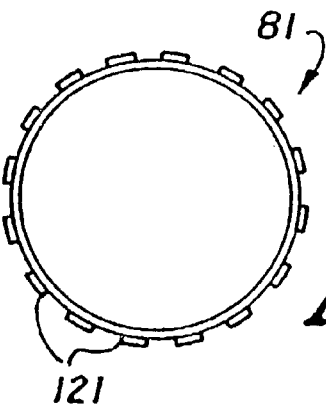
FIG. 4 is a partial elevational view of the distal portion of another embodiment of the penetrating catheter wherein the orientation element comprises an ultrasound transducer that is mounted in a fixed position.

In this embodiment the orientation element 81 comprises an imaging transducer fixedly mounted on the catheter 11, and in the embodiment illustrated in FIG. 3a, the imaging transducer is mounted on the distal tip section 55 just distally of the shoulder 57. In this embodiment, the imaging transducer 81 is a phased array transducer of the type shown schematically in FIG. 4a and is operative to image 360° about the catheter 11. This imaging transducer 81 comprises an annular array of individual crystals or elements 121 is coupled to a multiplex circuit 83 which is within the major section 51 of the catheter body 13 adjacent the shoulder 57, and the multiplex circuit 83 is in turn coupled to leads 85 which extend through the lead lumen 39 and a port 87 (FIG. 2) of the hub 21 to an imaging console 89. When activated, the imaging transducer emits ultrasound signals and receives back echos or reflections which are representative of the nature of the surrounding environment. The imaging transducer provides an imaging signal from which an image of the surrounding structure can be created by signal processing apparatus located in the imaging console 89 and viewed on a standard display screen located near the operating table on which the patient is positioned. In a preferred practice of this invention, the phased array transducer and the accompanying circuitry and the imaging console 89 may be obtained from Jomed, Inc. of Rancho Cordova, Calif.

Alternative Rotatable Transducer

Figure 4B:
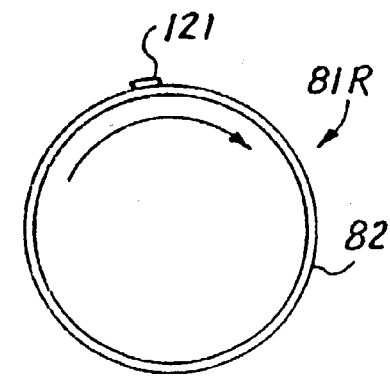

In an alternate embodiment of this invention, a rotatable imaging transducer 81r of the type illustrated schematically in FIG. 4b may be used. This alternative transducer 81r comprises one (or more than one) imaging element 121r that is mounted on a rotating shaft 82 that extends through a portion of the catheter body (e.g., and out of port 39) such that it can be rotated relative to the catheter body. Alternatively, it will be appreciated that this transducer 81r may be fixedly mounted within or upon the catheter body and the entire catheter body may be rotated in order to effect rotational movement of the transducer element 121r.

Alternative Separate Imaging Element Insertable Through a Lumen of the Catheter:

As an alternative to an imaging transducer mounted on or in the catheter, a separate imaging catheter (e.g., an IVUS catheter) or other elongate imaging member my be inserted through a lumen of the catheter body 13. The lumen through which such elongate imaging member may be inserted can be the same lumen 17 through which a guidewire may pass or may be a separate lumen. Examples of these types of catheters are found in U.S. Pat. No. 6,190,353 B1 (Makower, et al.) and/or in published PCT International Applications No. PCT/US98/07134 and PCT/US99/07115, the entireties of such patent and published PCT applications being expressly incorporated herein by reference.

Marker Structure

In this first embodiment (FIGS. 3a–3e), an imageable marker structure 101 is fixedly mounted on the catheter body 13 in a known circumferential orientation relative to the exit port 29. In the embodiment of FIG. 3a, the marker structure 101 is in the form cage (FIG. 3f) and the transducer 81 is within the cage. This marker structure 101 comprises a plurality of longitudinal members 103 and 103pp disposed at circumferentially spaced apart locations about a hollow interior space 105. The hollow space 105 receives the distal tip section 55 and the transducer 81, and the transducer 81 is an onboard transducer in that it is inseparable from and not removable from the catheter body 13. In this embodiment the transducer 81 is attached to or wrapped around the catheter body 13 and permanently retained by a suitable potting composition or adhesive. As shown in FIG. 3g, one of the longitudinal members 103pp is designated as the penetrator path indicating member and is positioned at a circumferential position that is axially aligned with the exit port 29 or otherwise positioned to be indicative of the path that will be followed by the tissue penetrator 85 as it is advanced from the catheter body 13 through the exit port 29. Thus, the imageable marker structure 101 forms on the image obtainable from the imaging signal from the imaging transducer a penetrator path indication that indicates the path that will be followed by the tissue penetrator when the tissue penetrator 85 exits from the catheter.

With the construction described above, the imaging transducer 81 and the marker 101 are both mounted on the distal tip section 55 which has a smaller cross sectional area than does the adjacent region of the major section 51 of the catheter body 13. Accordingly, the cross sectional area of the catheter body 13 at the region containing the imaging transducer 81 and the marker 101 can still be relatively small. Also, the exit location 29 is closely adjacent to the imaging transducer 81 and may be, for example, about 3 mm from the imaging transducer. This minimizes the likelihood of any significant torsional displacement of the exit location 29 relative to the marker 101 and imaging transducer 89. It may also be appreciated that the imaging transducer may be mounted such that the exit port is located directly at the point at which the transducer is affixed to the catheter, eliminating any displacement.

Figure 4A:
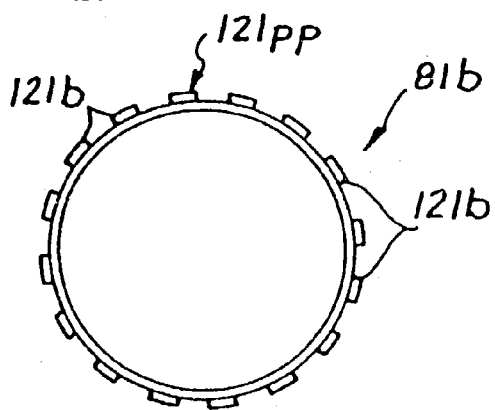

B. Second Embodiment: Catheter with Fixedly Mounted Imaging Transducer Useable Without Marker Structure FIG. 4 shows a second embodiment of the catheter 11a which is identical to the catheter 11 in all respects not shown or specified as being different herebelow. Portions of the catheter 11a corresponding to portions of the catheter 11 are designated by corresponding reference numerals followed by the letter a.

The primary difference between the catheters 11 and 11a is that the catheter 11a has no imageable marker structure 101. Instead, its imaging transducer 81a is mounted in a fixed position such that one particular element 121pp (or a group of particular elements) is/are designated as the penetrator path but rather is mounted in a fixed orientation within or upon the catheter such that a selected one (or selected ones) of the individual imaging elements 121 (e.g., crystals) of the phased array is positioned in known spacial relation to the path or plane of the path that will be followed by the tissue penetrator as exits from the catheter. This selected one (or ones) of the imaging elements 121 shall be referred to herein as the "penetrator-path-indicating element 121pp." The imaging elements 121, which may be adhered to the catheter body 13a, are mounted on the catheter 11 at known circumferential locations relative to the path that will be followed by a tissue penetrator as the tissue penetrator advances from the catheter 11 through the exit port 29a. The image obtained from the imaging signal from the imaging transducer 81a is thereby useable by the operator to rotationally orient the catheter 11 such that when the tissue penetrator subsequently exits from the catheter, the tissue penetrator will extend into the target as desired. Thus, because the imaging elements 121a are mounted on the catheter body 13 in fixed relationship to the catheter body and in a known circumferential orientation relative to the exit location 29a, the imaging transducer 81a can be used to provide an imaging signal for use in locating an adjacent blood vessel or other structure and identifying the angular orientation of the exit location. If desired, the imaging elements of the imaging transducer 81 of the catheter 11 can be oriented in the same fashion as described above for the catheter 11a. In this event, the only difference between the catheters 11 and 11a would be that the catheter 11 has an imaging marker 101 and the catheter 11a does not.

Figure 5:
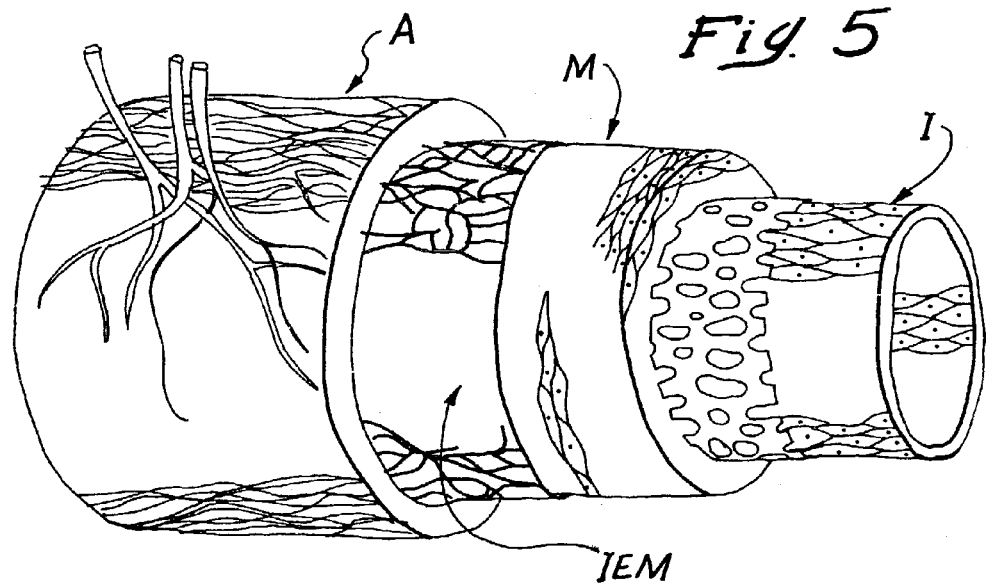
FIG. 5 is a diagram of an artery showing the three layers of tissue that comprise the artery wall.
Figure 5A:
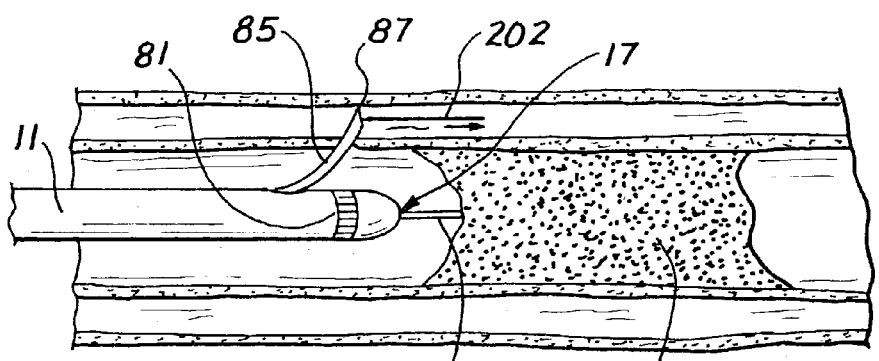
FIGS. 5a–5f are step-by-step diagrams showing one embodiment of a method of the present invention wherein a penetration catheter with on board orientation capabilities is used (with or without use of the orientation element) to initially place a guidewire into the sub-intimal space and wherein the same catheter is subsequently (with the orientation element) to cause reentry from the sub-intimal space into the vessel lumen, downstream of the obstruction.

FIG. 5a shows an image 151 of the catheter 11a (FIG. 4) in the resident blood vessel 143 in which that catheter is positioned, as well as an image of the target location 145, shown here as another blood vessel. Standard serial hash marks 300a, 300b, 300c and 300d are formed on the imaging screen as shown, generally dividing the screen into four quadrants. In this instance, the transducer 81b is fixedly mounted within the catheter 11a such that its penetrator path indicating transducer element 121pp is in the 12 o'clock position and aligned with the top array of hash marks 300a on the imaging screen. Thus, the top array of hash marks 300a serve as a visual indicator of the path that will be followed by the tissue penetrator 85 as it is advanced from the catheter 11a. In the showing of FIG. 5a, one can see that the top hash marks 300a do not enter the target location 145 and, thus, it can be concluded from this image that the tissue penetrator 85 is not properly aimed at the target location. However, by rotating the catheter 11a in the resident blood vessel 143, to the position shown in FIG. 5b, the top array of hash marks 300a is caused to pass directly through the target location 145, thus indicating to the operator that the tissue penetrator 85 can now be advanced from the exit port 29a to properly penetrate from the resident vessel 143 into the target location 145, as desired. Region 148 is defined an acceptable penetration zone.

Figure 5B:
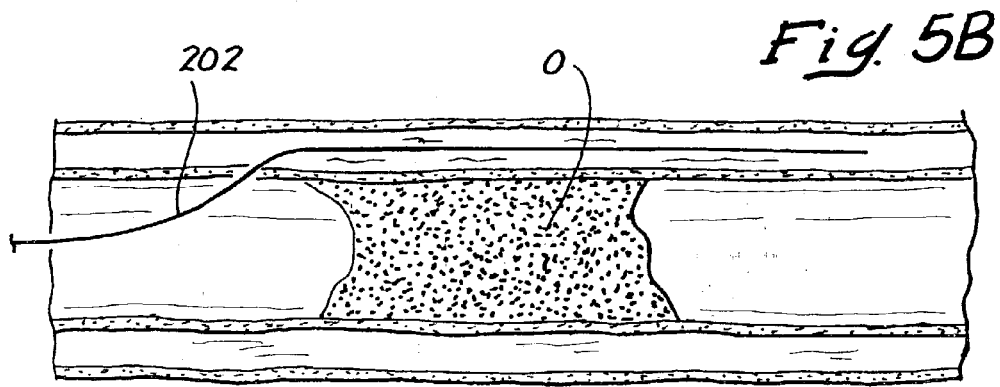
Figure 5C:
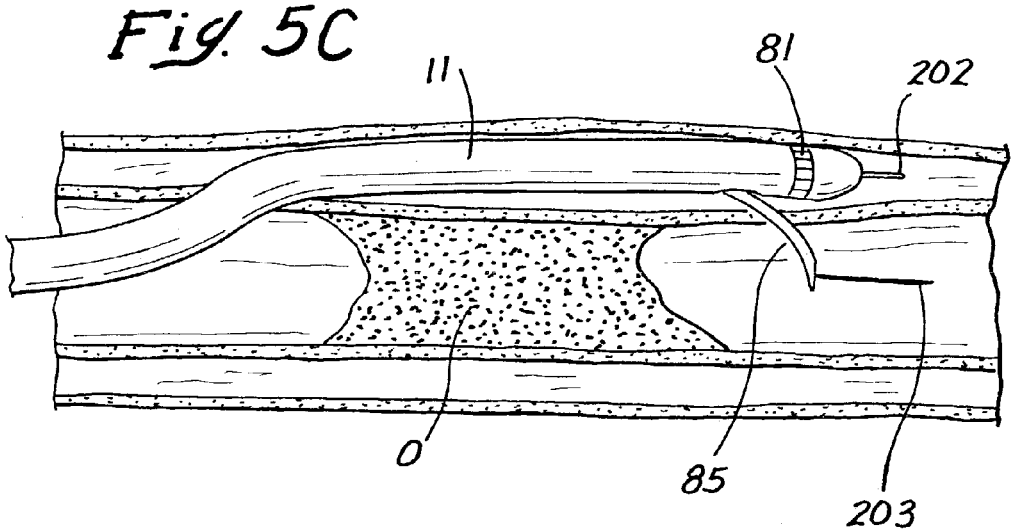
Figure 5D:
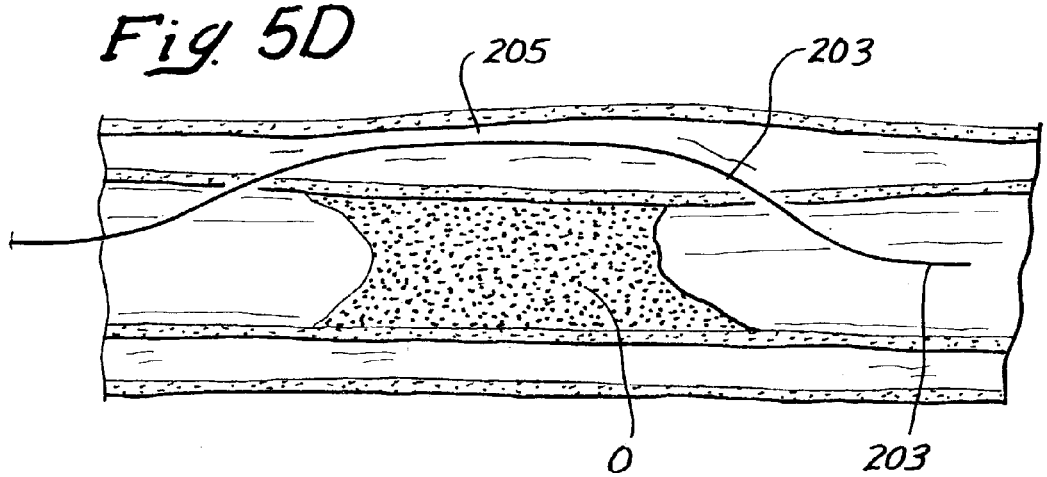
Figure 5E:
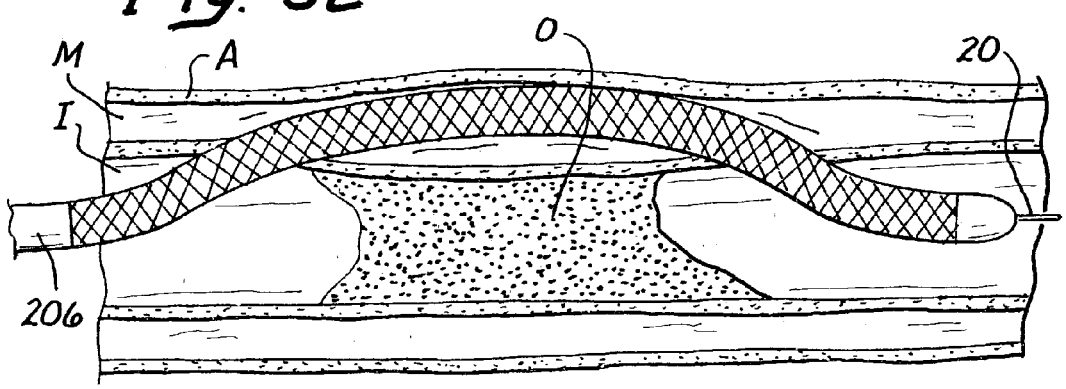
Figure 5F:
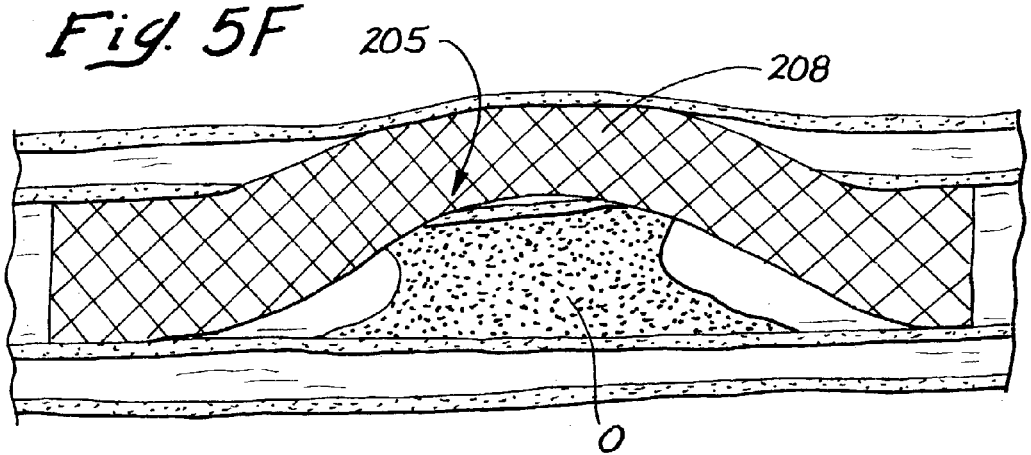

It will be appreciated that the electronically enhanced penetrator path indicating transducer 121pp may be used in conjunction with the hash marks 300a, 300b, 300c, and 300d shown in FIGS. 5a–5b and/or the line 146 shown in FIGS. 5c and 5d, thereby enabling the operator to utilize multiple indicia to determine the appropriateness of the size and distance range of the target location 145 before advancing the tissue penetrator 85. In this way, the operator is provided with a range of acceptable accuracy depending on the desired result and taking into account what procedures may be performed subsequently (i.e. placement of a connection device or other catheter devices).

With the construction described above, the imaging transducer 81 and the marker 101 are both mounted on the distal tip section 55 which has a smaller cross sectional area than does the adjacent region of the major section 51 of the catheter body 13. Accordingly, the cross sectional area of the catheter body 13 at the region containing the imaging transducer 81 and the marker 101 can still be relatively small. Also, the exit location 29 is closely adjacent to the imaging transducer 81 and may be, for example, about 5 mm from the imaging transducer. This minimizes the likelihood of any significant torsional displacement of the exit location 29 relative to the marker 101 and imaging transducer 89. It may also be appreciated that the imaging transducer may be mounted such that the exit port is located directly at the point at which the transducer is affixed to the catheter, illuminating any displacement.

C. Penetrating Catheters Wherein the Orientation Element Comprises a Sensor That Operates in Conjunction With a Sensing Field It will be appreciated that various other types of imaging or position sensing apparatus may be used as alternatives to the above-described imaging transducer 89/marker 101 combination to guide and orient the vessel wall penetrating catheter 11. For example, the vessel wall penetrating catheter 11 may incorporate an emitter that is useable in conjunction with an electromagnetic, potentiometric, or other electro-anatomical mapping and/or catheter guidance/positioning systems, such as those commercially available from or under development by Biosense Webster, Inc., Diamond Bar, Calif.; Cardiac Pathways Corporation, 995 Benicia Avenue, Sunnyvale, Calif. and/or Stereotaxis, Inc., 4041 Forrest Park Avenue, St. Louis, Mo. Examples of these types of catheter guidance or positioning systems are described in U.S. Pat. No. 5,820,568 (Willis), U.S. Pat. No. 5,931,818 (Werp et al.), U.S. Pat. No. 5,654,864 (Ritter et al.), U.S. Pat. No. 5,928,248 (Acker), U.S. Pat. No. 5,752,513 (Acker et al.), U.S. Pat. No. 5,558,091 (Acker et al.) And U.S. Pat. No. 5,833,608 (Acker), the entire disclosures of which are expressly incorporated herein by reference. The manner in which the catheter device 11 may be oriented using these types of electro-anatomical mapping systems is described in U.S. Provisional Patent Application No. 60/266,800, the entire disclosure of which is expressly incorporated herein by reference.

D. A First Procedure for Creating a Bypass Around a Total or Near-Total Arterial Obstruction:

As shown in FIG. 5, the wall of an artery typically consists of three layers, the tunica intima I ("intima"), tunica media M ("media") which is the thickest layer of the wall and the tunica adventitia A (adventitia). In some arteries an internal elastic membrane IEM is disposed between the media M and adventitia A.

FIGS. 5a through 5g show one method of the present invention wherein a sub-intimal bypass tract is created outside of the intima I and within the wall of the artery to allow blood flow around a total occlusion O.

In this method, a first elongate member or guidewire 200 is advanced into the artery upstream of the occlusion O. The proximal end of the first guidewire is then inserted into the distal opening 17 of the guidewire lumen 35 of the penetrating catheter 11 and the penetrating catheter 11 is then advanced over the first guidewire 200 to a position immediately upstream of the occlusion O. The penetrator 85 is then advanced laterally from the catheter 11 through the intima I and into the media M of the artery wall with its bevel cut distal opening 87 facing in the distal direction. The orientation element 81 of the catheter may optionally be used in this step if it is desired to enter a specific radial location on the artery wall however, if it is not desired to enter any specific location on the artery wall, the orientation element 81 need not necessarily be used in this step.

After the tip of the penetrator 85 has passed through the intima I of the artery wall, a second elongate member or guidewire 202 is advanced through the lumen 86 of the penetrator 85 and into the sub-intimal space (e.g., into tissue that forms aprt of the artery wall and/or into tissue or space located outside of the artery wall). This second guidewire 202 is then advanced in the distal direction past the occlusion O, creating a sub-intimal tract around the occlusion. This second guidewire 202 is advanced to a position where the distal tip of the second guidewire 202 is positioned outside of the intima I of the artery (e.g., in the sub-intimal space) and distal to the occlusion O. In some embodiments of the invention, an elongate member other than a guidewire may be initially used to create the sub-intimal tract. Interventional cardiologists skilled in the art will appreciate and understand the types of alternative elongate members that may be used in this step including an apparatus known as an "olive", a laser wire, an elongate radiofrequency electrode, or any other elongate member suitable for boring or advancing through tissue. If an alternative type of elongate member is used instead of the second guidewire 202 to form the sub-intimal tract, such alternative elongate member may be removed and replaced with the second guidewire 202 after the suc-intimal tract has been formed as illustrated in FIG. 5b. Thereafter, the penetrator 85 is retracted into the penetrating catheter 11 and the catheter 11 and first guidewire 200 are removed, leaving the second guidewire 202 in place within the sub-intimal tract as shown in FIG. 5b.

As shown in FIG. 5c, the proximal end of the second guidewire 202 is then introduced into the distal opening 17 of the guidewire lumen 35 of the penetrating catheter 11 and the catheter 11 is advanced over the second guidewire 202, through the sub-intimal tract, to a position where the distal end of the catheter 11 is located outside of the intima I and distal to the occlusion O. In some cases, it may be desirable to enlarge the diameter of the sub-intimal tract before advancing the catheter 11 through it. Such enlargement of the sub-intimal tract may be accomplished by passing a PTCA catheter over the wire 202 and inflating the PTCA balloon to dilate the tract, or may any other suitable tract enlarging, dilating or debulking instrument that may be passed over the second guidewire 202.

The orientation element 81 of the catheter 11 is then used to precisely rotate the catheter 11 into an orientation that will ensure that the penetrator 85 will enter the lumen of the artery downstream of the occlusion O. After the catheter 11 has been placed in the correct rotational orientation with the aid of the orientation element, the penetrator 85 is advanced into the artery lumen and a third guidewire 204 is then advanced through the lumen 86 of the penetrator 85 and into the lumen of the artery downstream of the occlusion O, as shown in FIG. 5C.

Thereafter, the penetrating catheter 11 and second guidewire 202 are removed, leaving the third guidewire 204 in place and extending through the sub-intimal tract 205, as shown in FIG. 5D. The occlusion O has now been successfully crossed.

The proximal end of the third guidewire 204 is then introduced into the guidewire lumen of a PTCA balloon catheter 206 having a stent 208 mounted thereon in a radially collapsed state. The PTCA balloon catheter 206 and stent 208 are then advanced over the third guidewire 204 to a position where the distal end of the stent 208 is in the lumen of the artery distal to the obstruction O, the proximal end of the stent 208 is in the lumen of the artery proximal to the obstruction O, and the mid-portion of the stent 208 extends through the sub-intimal tract 205. Thereafter, the balloon of the PTCA catheter 206 is inflated to radially expand the stent 208 such that the ends of the stent 208 firmly coapt with the intima I of the artery and the mid-portion of the stent 208 provides a scaffold which maintains the sub-intimal tract 205 in an open condition capable of carrying blood past the obstruction 0. Thereafter, as shown in FIG. 5 F., the PTCA catheter 206 is removed leaving the radially expand stent 208 in place, with blood flowing through the sub-intimal tract 205 around the obstruction 0. It will be appreciated that, although in this example a PTCA balloon catheter 206 having a pressure-expandable stent 208 mounted thereon was used, self-expanding stents which are well-known in the art may also be used with stent delivery catheters rather than a balloon catheter. Examples of commercially available pressure-expandable stents that are usable for this purpose include the Bx Velocity™ stents available from Cordis Corporation, Miami, Fla.; Jomed Covered Stent-Graft available from Jomed, Inc., Rancho Cordova, Calif. and the Multi-Link™ stents available from Guidant Corporation, Santa Clara, Calif. Examples of self-expanding stents that are commercially available and usable for this purpose include SmartStent™ stents (covered or uncovered) available from Cordis Corporation. Miami, Fla.; Radius™ stents available from Boston Scientific/Scimed Inc., Maple Grove, Minn. and Hemobahn™ endoprostheses (stents lined with expanded PTFE grafts) available from W. L. Gore, Flagstaff, Ariz.

Figure 6:
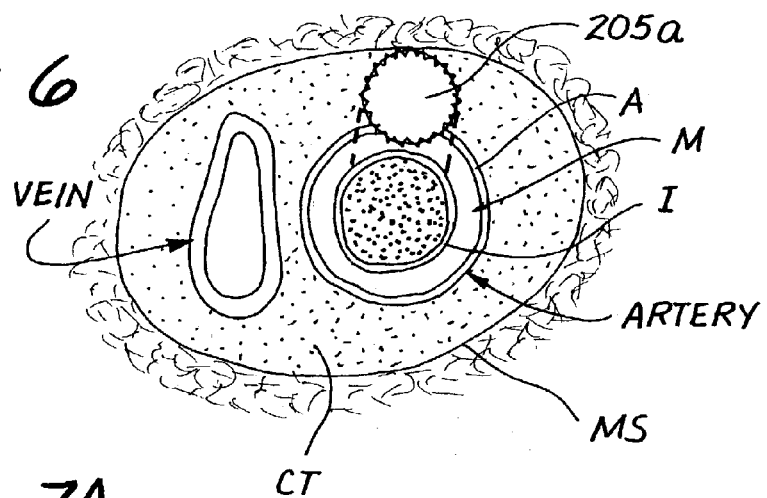
FIG. 6 is a diagram of a neurovascular bundle wherein an artery and vein are surrounded by a membranous sheath and wherein a procedure of the present invention has been used to create a bypass channel around an obstruction in the artery, such bypass channel being at least partially outside of the artery wall but inside of the membranous sheath.

It will be appreciated that all although the figures show sub-intimal tracts 25 that do not penetrate out of the adventitia A of the artery, in some instances the methods of the present invention will be used in a manner that causes the sub-intimal tract 205 to extend outside of the adventitia A and into space or tissues surrounding the artery. Procedures of this type have previously been described in U.S. Pat. No. 6,231,587, of which this is a continuation in part. In cases where the sub-intimal tract 205 does extend outside of the adventitia A of the artery, it will be preferable for the sub-intimal passageway 205 to be surrounded by tissue that is sufficiently dense to contain any blood that leaks from the tract 205 thereby preventing the formation of a hematoma or bleeding into the surrounding tissue. However, in cases where the surrounding tissue is not sufficiently dense to act in this manner, a covered stent or stent-graft may be placed in the sub-intimal tract 205 to contain the blood flow passing through the sub intimal tract 205. One example of an anatomical area where sub-intimal tracts 205 that extend outside of the adventitia A may be used is in the brain where, as shown in FIG. 6, some arteries and veins are typically encased in connective tissue C T and surrounded by a membranous sheath MS. In such instances, a sub-intimal tract 205A, as shown in FIG. 6, may enter the connective tissue CT but still be within the membranous sheath MS such that any leakage of blood from the sub-intimal tract 205 will be contained within the membranous sheath MS.

Figure 7A:
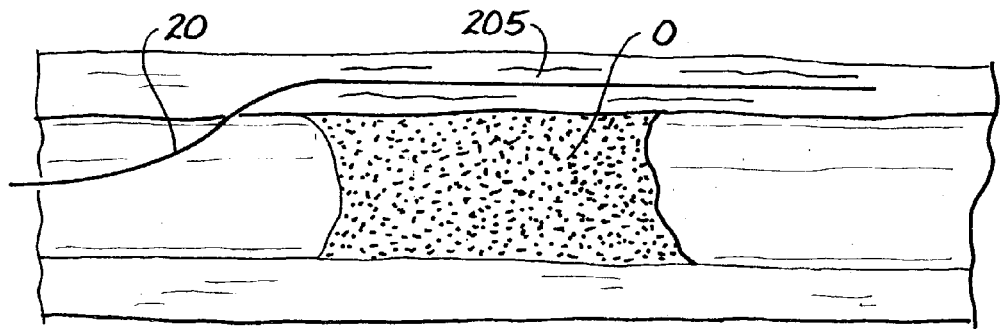
FIGS. 7A–7E are step-by-step diagrams showing another embodiment of a method of the present invention wherein a guidewire is initially advanced into the sub-intimal space and past the lesion and wherein a penetration catheter having an orientation element is advanced over the guidewire and used (with concomitant use of its orientation element) to cause reentry from the sub-intimal space into the vessel lumen, downstream of the obstruction.
Figure 7B:
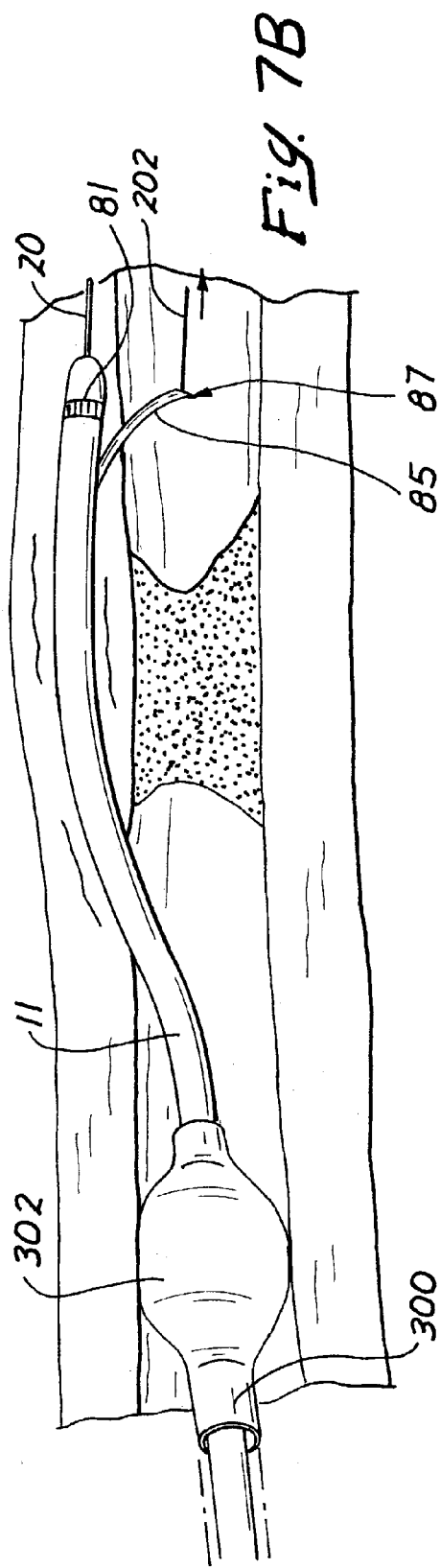

Another embodiment of the method of the present invention is shown in FIGS. 7A–7E. In this embodiment of the method, a first guidewire 200 is percutaneously inserted and advanced through the vasculature to a position where the distal end of the first guidewire 200 is just proximal to the obstruction O that used to be bypassed. Upon determining that the first guidewire 200 cannot be passed through the obstruction O, the operator uses standard technique in accordance with the prior art to force the first guidewire 200 through the intima I and past the obstruction O forming a sub-intimal tract 205. However, the distal end of the first guidewire 200 remains positioned outside the intima I and outside the lumen of the artery, as shown in FIG. 7A. This type of "trapped" guidewire is not uncommon in the clinical practice of interventional cardiology. This method, as described herebelow provides a novel method of dealing with such trapped guidewire to effect the desired bypassing of the obstruction O.

In accordance with this invention, and optional balloon catheter of 300 is then advanced over the first guidewire 200 to a position in that is proximal to the obstruction 0. This optional balloon catheter 300 may be used to stop blood flow through the artery during the procedure or during portions of the procedure. The ability to stop blood flow through the artery during the procedure may be particularly useful when the operator is concerned that the wall of the artery may be perforated inadvertently or where the operator intends for the sub-intimal tract 205 to extend outside of the adventitia A as may arise in blood leakage from the artery. In such event, inflation of the balloon 302 of the balloon catheter 300 will serve to stop the flow of blood during the procedure until any concern of vessel wall perforation has passed or until a covered stent, stent graft or other hemostatic apparatus is placed in the sub-intimal tract 205 to prevent bleeding outside of the artery.

After the optional balloon catheter 300 has been positioned, a penetrating catheter 11 of the type described hereabove is a danced over the first guidewire 200 through the lumen of the balloon catheter 300 and into the sub-intimal tract 205 to a position where the distal end of the penetrating catheter 11 is distal to the obstruction O and outside of the lumen of the artery. Thereafter, the orientation element 81 of the catheter 11 is used to precisely rotate the catheter 11 to a position where the penetrator 85 will advance into the lumen at all of the artery. Thereafter, as shown in FIG. 7 the, the penetrator 85 is advanced from the catheter 11 and into the lumen of the artery. A second guidewire 202 is then advanced through the lumen of the penetrator 85, out of its distal end opening 87 and into the lumen of the artery, downstream of the obstruction O. The penetrator 85 is then retracted into the penetrating catheter 11 and the penetrating catheter 11 is removed along with the first guidewire 202, leaving the second guidewire 204 in place such that it extends through the sub-intimal tract 205 and into the lumen of the artery downstream of the obstruction O. The obstruction O has now been successfully crossed.

Figure 7C:
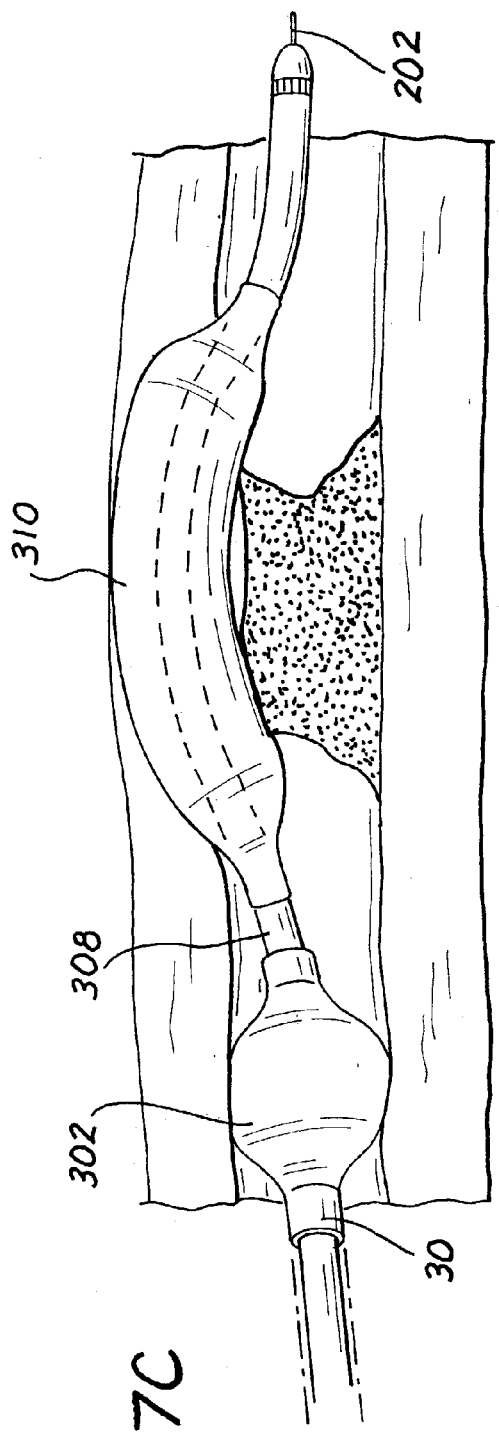
Figure 7D:
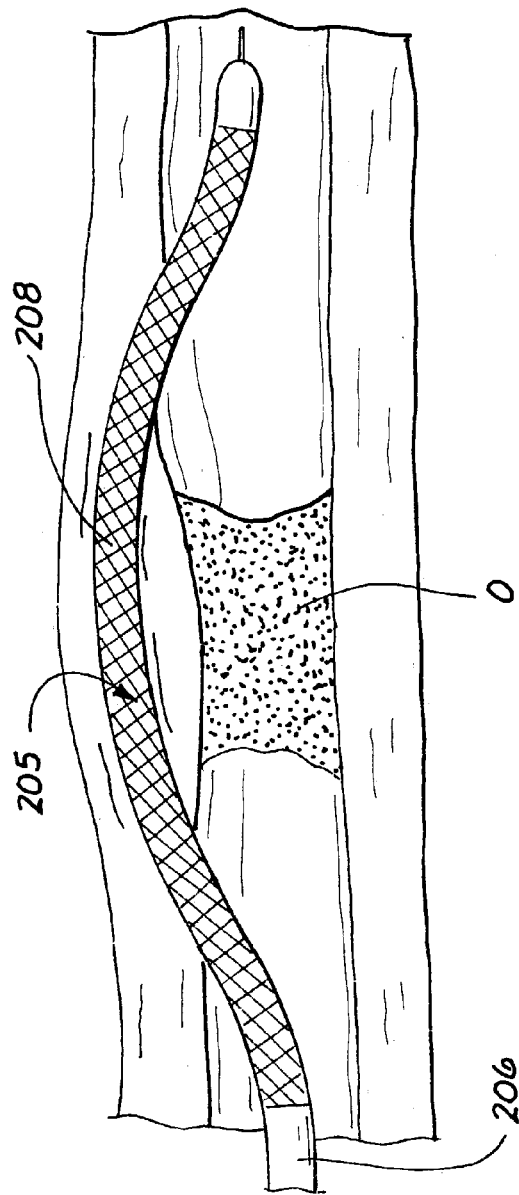

Thereafter, as shown in FIG. 7C an optional tract enlarging catheter 308 of the types described hereabove may optionally the advanced over the second guidewire 204 and used to dilate or otherwise enlarge the sub intimal tract 205. In some cases, this tract enlarging catheter 308 may be a balloon catheter such as a PTCA catheter and its balloon 310 may be inflated within the tract 205 so as to dilate the tract and compress the adjacent obstruction O.

Figure 7E:
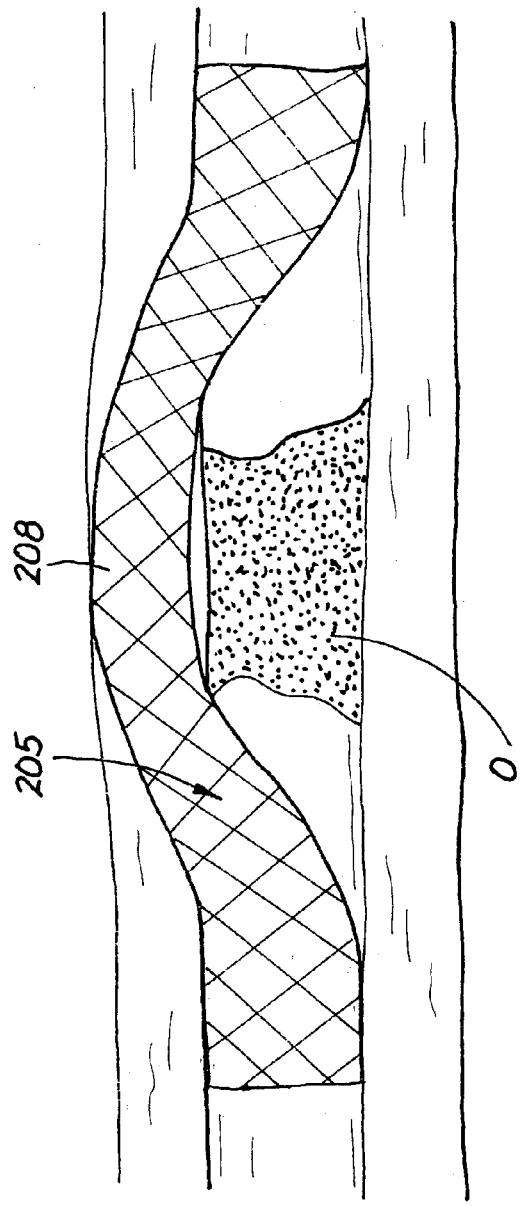

After any optional enlargement of the tract 205 has been completed, the optional tract enlarging catheter 308 is removed and a PCTA catheter 206 and stent 208 or other type of stent deliver catheter and stent as described above, are advanced over the second guidewire 202 to a position where the distal end of the radially collapsed stent 208 is in the lumen of the artery distal to the obstruction O, the proximal end of the stent 208 is in the lumen of the artery proximal to the obstruction O, and the mid-portion of the stent 208 extends through the sub-intimal tract 205. Thereafter, the balloon of the PTCA catheter 206 is inflated to radially expand the stent 208 such that the ends of the stent 208 firmly coapt with the intima I of the artery and the mid-portion of the stent 208 provides a scaffold which maintains the sub-intimal tract 205 in an open condition capable of carrying blood past the obstruction 0. Thereafter, as shown in FIG. 7E, the PTCA catheter 206 (and the optional balloon catheter 300, if used) is/are removed leaving the radially expanded stent 208 in place, with blood flowing through the sub-intimal tract 205 around the obstruction 0.

Figure 8A:
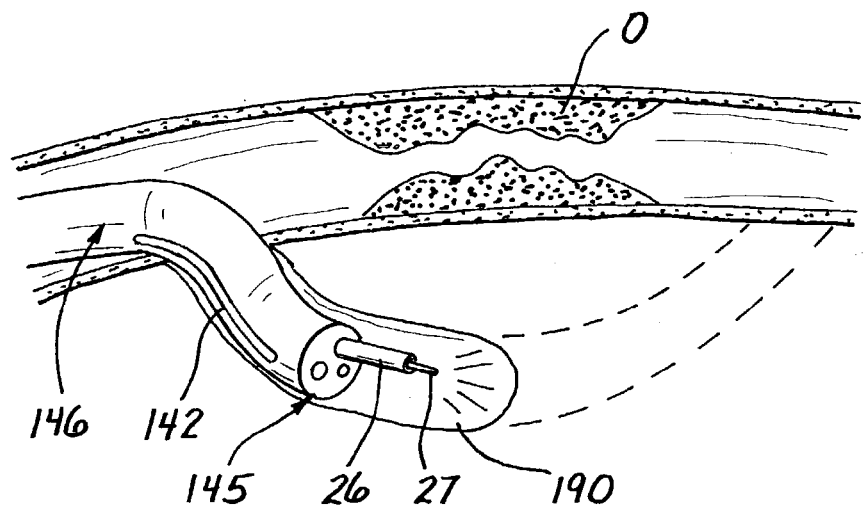
FIGS. 8a and 8b are step by step diagrams of yet another embodiment of a method of the present invention wherein a deflectable tipped penetrating catheter having an on board orientation element is used to create a bypass channel that extends outwardly through the wall of an artery upstream of an obstruction, through tissue adjacent to the artery and back into the lumen of the artery downstream of the obstruction.
Figure 8B:
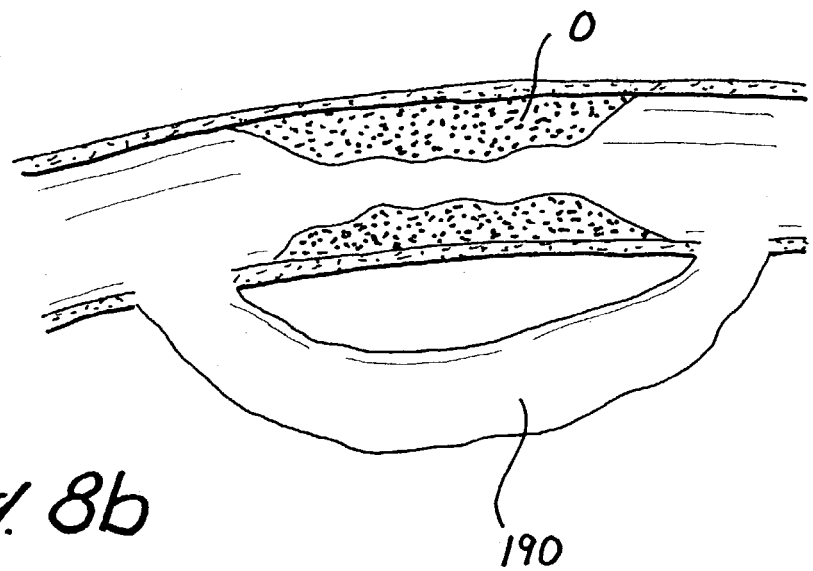

FIGS. 8A and 8B are reproduced from U.S. Pat. No. 6,068,638, of which this is a continuation-in-part. These figures show another alternative procedure of the present invention wherein a penetrating catheter 146 having a deflectable tip is used to create a passageway 190 around an obstruction O in an artery. This passageway 190 extends outside of the artery wall in through tissue (e.g., myocardium or muscle) that is adjacent to the artery. This penetration catheter 146 has a deflectable distal tip 145 with an actively controlled shape memory material 142. Here the catheter 146 itself is shown tunneling through surrounding tissue utilizing probe 27 and sheath 29 to guide the way. Ultimately, the catheter 146 creates a tunnel 190 which can be used to allow flow from one point to another point in artery, as shown. It will be appreciated that an orientation element 81 as described herein may be used to guide and control the placement of the catheter 146 and the deflection of the tip 145 to ensure that the probe 27 will re-enters the lumen of the artery, downstream of the obstruction.

Although exemplary embodiments of the invention have been shown and described, many changes, modifications and substitutions may be made by those having ordinary skill in the art without necessarily departing from the spirit and scope of this invention. Specifically, elements or attributes described in connection with one embodiment may also be used in connection with another embodiment provided that the inclusion or use of such element or attribute would not render the other embodiment in which it is incorporated unuseable or otherwise undesirable for an intended application. Accordingly, all such additions, deletions, modifications and variations to the above-described embodiments are to be included within the scope of the following claims.

What is claimed is:

1. A method for bypassing an obstruction in a blood vessel having a wall and a subintimal tract that has been formed in said wall adjacent to the obstruction, said method comprising the steps of:
   A. providing a catheter device that comprises i) an elongate, flexible catheter body having a distal end, ii) a lumen extending longitudinally through at least a distal portion of the catheter body to permit the catheter device to be advanced over an elongate member, iii) a penetration member having a distal end, said penetration member being advanceable on an advancement trajectory and iv) an orientation element useable to enable the operator to determine the rotational orientation of the catheter body relative to the advancement trajectory of the penetrator to enable the operator to adjust the rotational orientation of the catheter body prior to advancement of the penetrator from the catheter body so that subsequent advancement of the penetrator on the advancement trajectory will cause the penetrator to advance to a target location;
   B. advancing the catheter device into the subintimal tract to a position where to distal end of the catheter body is positioned in the subintimal tract distal to the obstruction;
   C. rotationally orientating the catheter body with the aid of the orientation element such that, when the penetration member is subsequently advanced from the catheter body, the penetration member will enter the lumen of the anatomical conduit distal to the obstruction;
   D. advancing the penetration member from the catheter body and into the lumen of the anatomical conduit distal to the obstruction;
   E. providing an elongate member having a distal end; and,
   F. advancing the second elongate member trough the lumen of the penetration member to a position where the distal end of the second elongate member is within the lumen of the anatomical conduit distal to the obstruction.

2. A method according to claim 1 further comprising the step of:
   removiug the catheter device, leaving the elongate member in place.

3. A method according to claim 2 further comprising the steps of:
   advancing a stent delivery catheter with a stent over the third elongate member;
   deploying and radially expanding the stent; and,
   removing the stern delivery catheter, leaving the stent in place, such that fluid may flow from the lumen of the anatomical conduit proximal to the obstruction, through the lumen of the stent and back into the lumen of the anatomical conduit distal to the obstruction.

4. A method according to claim 2 further comprising the steps of:

advancing a dilator over the elongate member; and using the dilator to dilate the subintimal tract.

5. A method according to claim 1 wherein the blood vessel is an artery.

6. A method according to claim 5 wherein the artery is located in the leg of a human subject.

7. A method according to claim 5 wherein the wall of the artery is substantially surrounded by a membrane and wherein the subintimal tract is located within the membrane but outside of the artery wall.

8. A method according to claim 1 wherein the blood vessel is a coronary artery.

* * * * *

UNITED STATES PATENT AND TRADEMARK OFFICE
CERTIFICATE OF CORRECTION

PATENT NO. : 7,179,270 B2  Page 1 of 1
APPLICATION NO. : 10/370231
DATED : February 20, 2007
INVENTOR(S) : Joshua Makower It is certified that error appears in the above-identified patent and that said Letters Patent is hereby corrected as shown below:

Column 14, line 52, "F. advancing the second elongate member trough the" should be changed to --F. advancing the elongate member through the--

Column 14, line 66, "removing the stern delivery catheter, leaving the stent in" should be changed to --removing the stent delivery cateter, leaving the stent in--

Signed and Sealed this

Twentieth Day of May, 2008

JON W. DUDAS
*Director of the United States Patent and Trademark Office*